(12) United States Patent
Lee et al.

(10) Patent No.: US 10,172,605 B2
(45) Date of Patent: Jan. 8, 2019

(54) SURGICAL RETRACTOR ASSEMBLY

(71) Applicant: AJOU UNIVERSITY INDUSTRY-ACADEMIC COOPERATION FOUNDATION, Suwon-si, Gyeonggi-do (KR)

(72) Inventors: Kil Yeon Lee, Seoul (KR); Moon Gu Lee, Gwacheon-si (KR); Yong Ho Jeon, Suwon-si (KR); Chan Woo Lee, Changwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 463 days.

(21) Appl. No.: 14/760,408

(22) PCT Filed: Jun. 17, 2013

(86) PCT No.: PCT/KR2013/005296
§ 371 (c)(1),
(2) Date: Jul. 10, 2015

(87) PCT Pub. No.: WO2014/109441
PCT Pub. Date: Jul. 17, 2014

(65) Prior Publication Data
US 2015/0351855 A1    Dec. 10, 2015

(30) Foreign Application Priority Data
Jan. 11, 2013    (KR) .................. 10-2013-0003676

(51) Int. Cl.
A61B 17/02    (2006.01)
A61B 17/00    (2006.01)
A61B 90/00    (2016.01)

(52) U.S. Cl.
CPC .............. *A61B 17/0218* (2013.01); *A61B 2017/00345* (2013.01); *A61B 2017/00349* (2013.01);
(Continued)

(58) Field of Classification Search
CPC .......... A61B 2017/12086; A61B 17/52; A61B 34/73; A61B 2050/21
See application file for complete search history.

(56) References Cited

U.S. PATENT DOCUMENTS 7,169,104 B2 *  1/2007  Ueda ...................... A61B 34/73
                                                    128/899
8,038,612 B2 * 10/2011  Paz ........................ A61B 1/3132
                                                    600/210

(Continued)

FOREIGN PATENT DOCUMENTS

JP    2004-358024 A    12/2004
JP    2009-540934 A    11/2009
(Continued)

OTHER PUBLICATIONS

International Search Report dated Sep. 10, 2013, issued to the corresponding International Application No. PCT/KR2013/005296.
(Continued)

*Primary Examiner* — Anu Ramana
(74) *Attorney, Agent, or Firm* — Stein IP, LLC (57) ABSTRACT

The present subject matter relates to a surgical retractor. The surgical retractor includes: a movable body part which is inserted into a body; a hook part which is connected with the movable body part inside the body and pulls out an object that is inside of the body; and an operating part for operating, from the outside of the body, the movement of the movable body part inside the body.

4 Claims, 6 Drawing Sheets

(52) U.S. Cl.
CPC ............... *A61B 2017/00876* (2013.01); *A61B 2017/0287* (2013.01); *A61B 2090/08021* (2016.02)

(56) References Cited

U.S. PATENT DOCUMENTS

| | | | |
|---|---|---|---|
| 8,343,171 B2* | 1/2013 | Farritor | A61B 19/2203 318/568.12 |
| 2004/0138552 A1 | 7/2004 | Harel et al. | 600/407 |

FOREIGN PATENT DOCUMENTS

| | | |
|---|---|---|
| JP | 2010-220876 A | 10/2010 |
| KR | 20-2007-0000408 U | 4/2007 |
| WO | WO 2011/107317 A1 | 9/2011 |
| WO | WO 2012/033925 A1 | 3/2012 |

OTHER PUBLICATIONS

Sun Jin Park et al., "Notes Cholecystectomy using a hook-attached magnetic traction device in a porcine model", Dept. of Surgery, School of Medicine, Kyung Hee Univ., R.O. Korea, pp. 1-10.

Sun Jin Park et al., "A novel hook-attached magnetic traction/retraction for non-invasive surgery", Dept. of Surgery, School of Medicine, Kyung Hee Univ., R.O. Korea, p. 1.

Sun Jin Park et al., "Notes Cholecystectomy using a hook-attached magnetic traction device in a porcine model", Department of Surgery and Internal Medicine, School of Medicine, Kyung Hee University, Department of Mechanical Engineering, College of Engineering, Ajou University, slides 1-8.

* cited by examiner

SURGICAL RETRACTOR ASSEMBLY

CROSS-REFERENCE TO RELATED APPLICATIONS

This application is a national stage of International Application No. PCT/KR2013/005296, filed Jun. 17, 2013, which claims the benefit of priority to Korean Application No. 10-2013-0003676, filed Jan. 11, 2013, in the Korean Intellectual Property Office, the disclosures of which is incorporated herein by reference.

BACKGROUND OF THE INVENTION

Field of the Invention

The present invention relates to a surgical retractor. More particularly, the present invention relates to a surgical retractor which can remotely pull organs or tissues inside a body without a need for a separate incision for traction of the organs or tissues.

Description of Related Art Including Information Disclosed Under 37 CFR 1.97 and 1.98

Generally, traditional laparotomy for treating a patient requires a large incision and causes much blood loss during surgery, which slows recovery of the patient after surgery and leaves a big scar, thus negatively affecting the patient's daily life. To overcome this disadvantage of laparotomy, recently, novel surgical techniques such as minimally invasive surgery (MIS) using a laparoscope have been developed.

One example of the related art is disclosed in Korean Utility Model Publication No. 20-2007-0000408 (published on Apr. 6, 2007 and entitled "The structure of Auvard Weighted Speculum adapted LED light with contamination prevention function").

Conventionally, a separate incision is required for traction of organs or tissues inside a body, thereby causing increase in number of incisions and slow recovery after surgery.

Therefore, there is a need for an improved surgical retractor capable of overcoming this problem.

BRIEF SUMMARY OF THE INVENTION

The present invention has been conceived to solve such a problem in the art and an aspect of the present invention is to provide a surgical retractor which can remotely pull organs or tissues inside a body without a need for a separate incision for traction of the organs or tissues.

In accordance with an aspect of the present invention, a surgical retractor includes: a movable body portion inserted into a body; a hook portion connected to the movable body portion inside the body and pulling an object inside the body; and an operating portion operating the movable body portion within the body from outside of the body.

Preferably, the operating portion includes a magnet, and the movable body portion includes a material capable of being attracted to the magnet to be moved inside the body in association with movement of the operating portion.

More preferably, the operating portion further includes a housing and a ball rotatably disposed on one surface of the housing, and the magnet is mounted within the housing.

More preferably, the magnet is detachably mounted in a mounting jaw formed within the housing.

More preferably, the hook portion includes: a string connected to the movable body portion at one side thereof; and a hook connected to the other side of the string and hooking the object.

More preferably, when the movable body portion is moved inside the body through the movement of the operating portion outside the body, the object is pulled by the hook due to tension created in the string connected to each of the hook hooking the object and the movable body portion.

More preferably, the hook has a fish hook shape.

According to the present invention, the surgical retractor allows organs or tissues inside a body to be pulled by a hook and a string inserted in advance of surgical instruments, thereby eliminating a need for a separate incision for traction of organs or tissues.

In addition, according to the present invention, the surgical retractor can remotely operate the movable body portion placed within the body using the operating portion placed outside the body and thus allows the hook to easily approach organs or tissues during surgery while securing a clear view for surgery.

Further, according to the present invention, the surgical retractor can achieve traction of organs or tissues inside the body only by the string and the hook, and thus allows simplification of a structure of the retractor inserted into the body, thereby reducing time and costs consumed to disinfect or replace the retractor.

DETAILED DESCRIPTION OF THE INVENTION

Hereinafter, embodiments of the present invention will be described in detail with reference to the accompanying drawings. It should be noted that the drawings are not to precise scale and may be exaggerated in thickness of lines or size of components for descriptive convenience and clarity only.

In addition, the terms used herein are defined by taking functions of the present invention into account and can be changed according to user or operator custom or intention. Therefore, definition of the terms should be made according to the overall disclosure set forth herein.

Figure 1:
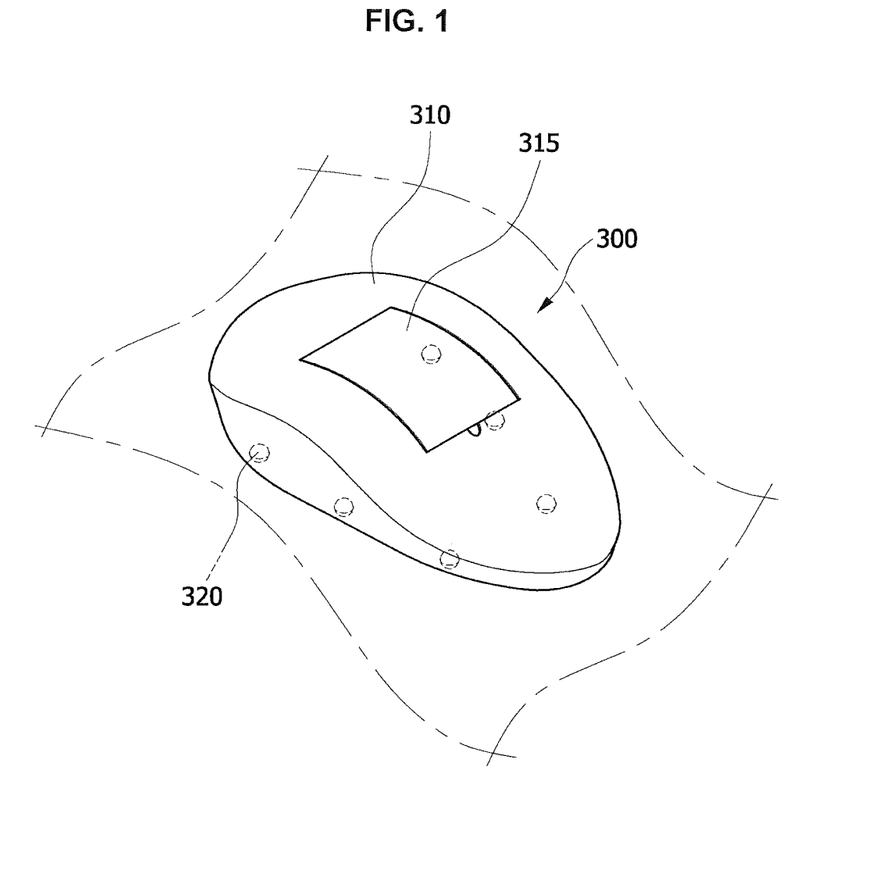
FIG. 1 is a perspective view of an operating portion according to one embodiment of the present invention.

FIG. 1 is a perspective view of an operating portion according to one embodiment of the present invention; FIG.

Figure 4:
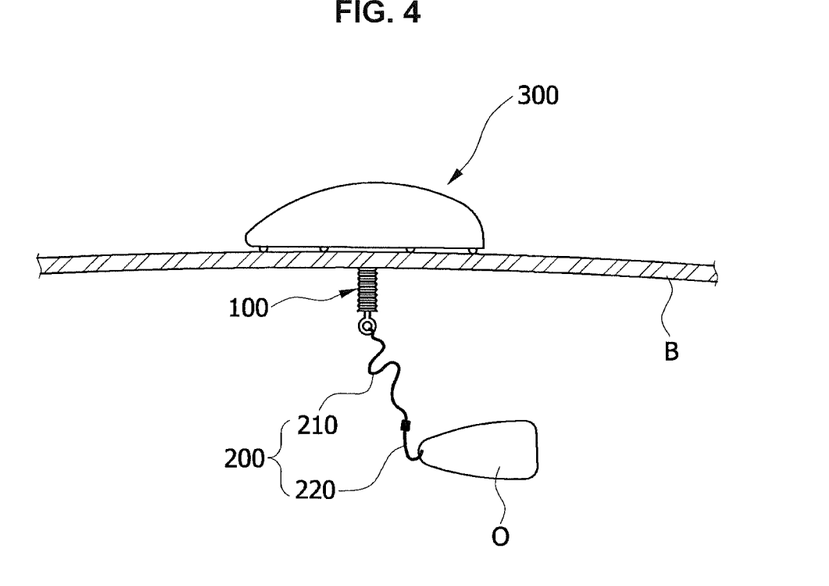
FIG. 4 is a side view of the retractor according to the embodiment of the present invention, with an object hooked by a hook portion.
Figure 5:
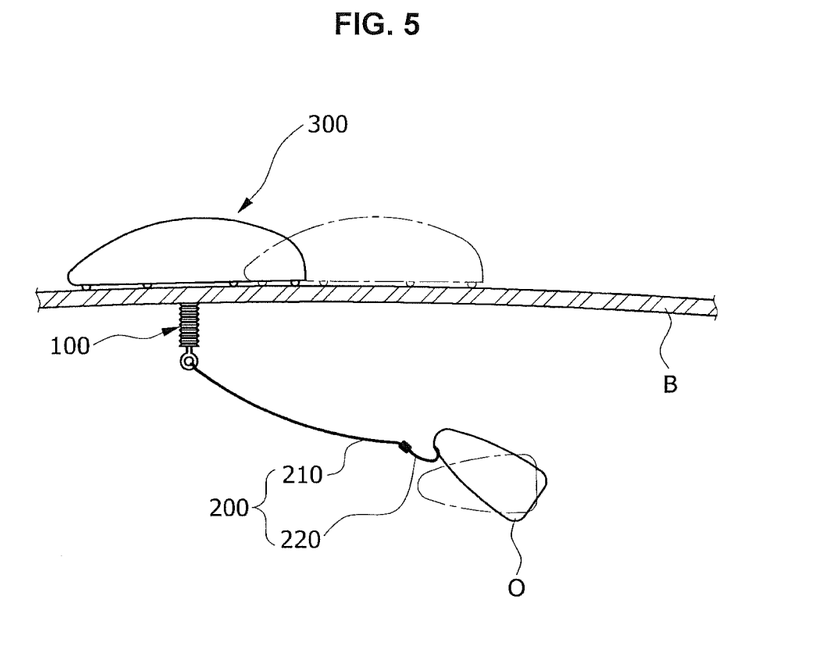
FIG. 5 is a side view of the retractor according to the embodiment of the present invention, with the object pulled by the hook portion through movement of the operating portion.
Figure 6:
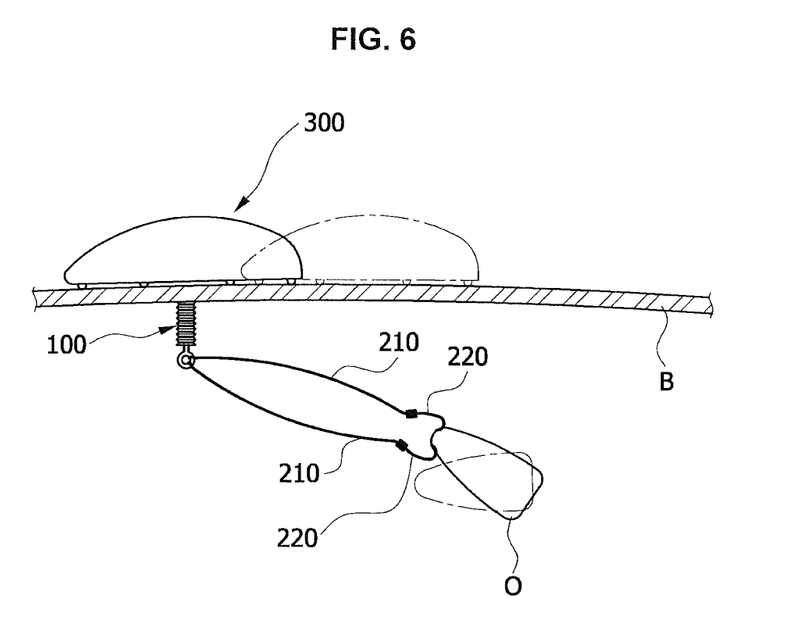
FIG. 6 is a side view of the retractor according to the embodiment of the present invention, with the object pulled by a plurality of hook portions through movement of the operating portion.

2 is a perspective view showing an inside of the operating portion according to one embodiment of the present invention; FIG. 3 is a schematic view of a retractor according to one embodiment of the present invention; FIG. 4 is a side view of the retractor according to the embodiment of the present invention, with an object hooked by a hook portion; FIG. 5 is a side view of the retractor according to the embodiment of the present invention, with the object pulled by the hook portion through movement of the operating portion; and FIG. 6 is a side view of the retractor according to the embodiment of the present invention, with the object pulled by a plurality of hook portions through movement of the operating portion.

Figure 2:
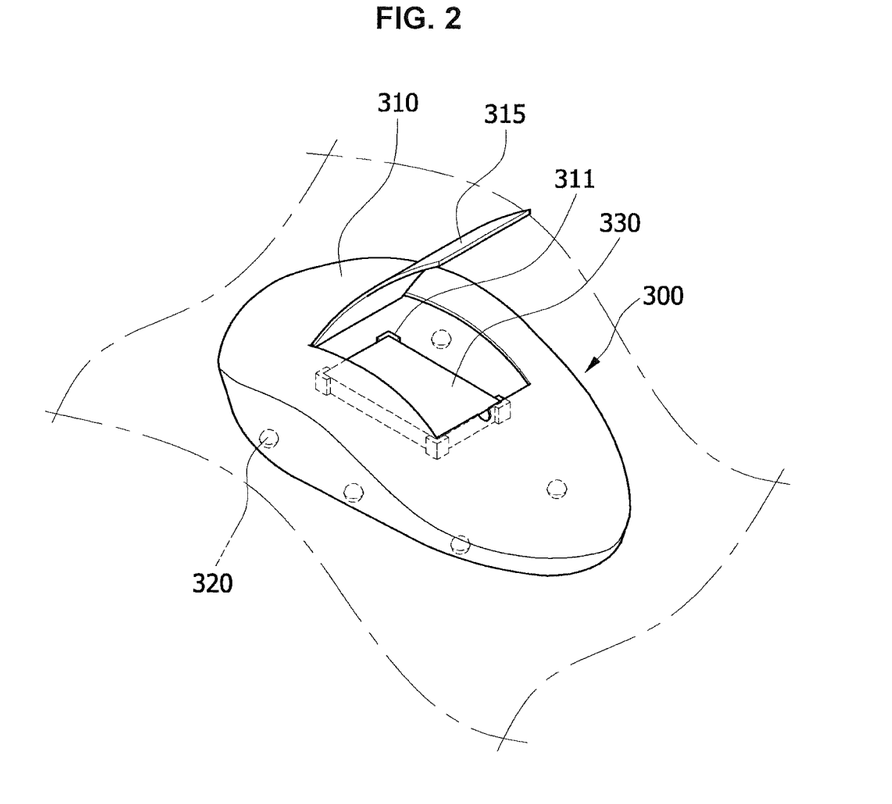
FIG. 2 is a perspective view showing an inside of the operating portion according to one embodiment of the present invention.
Figure 3:
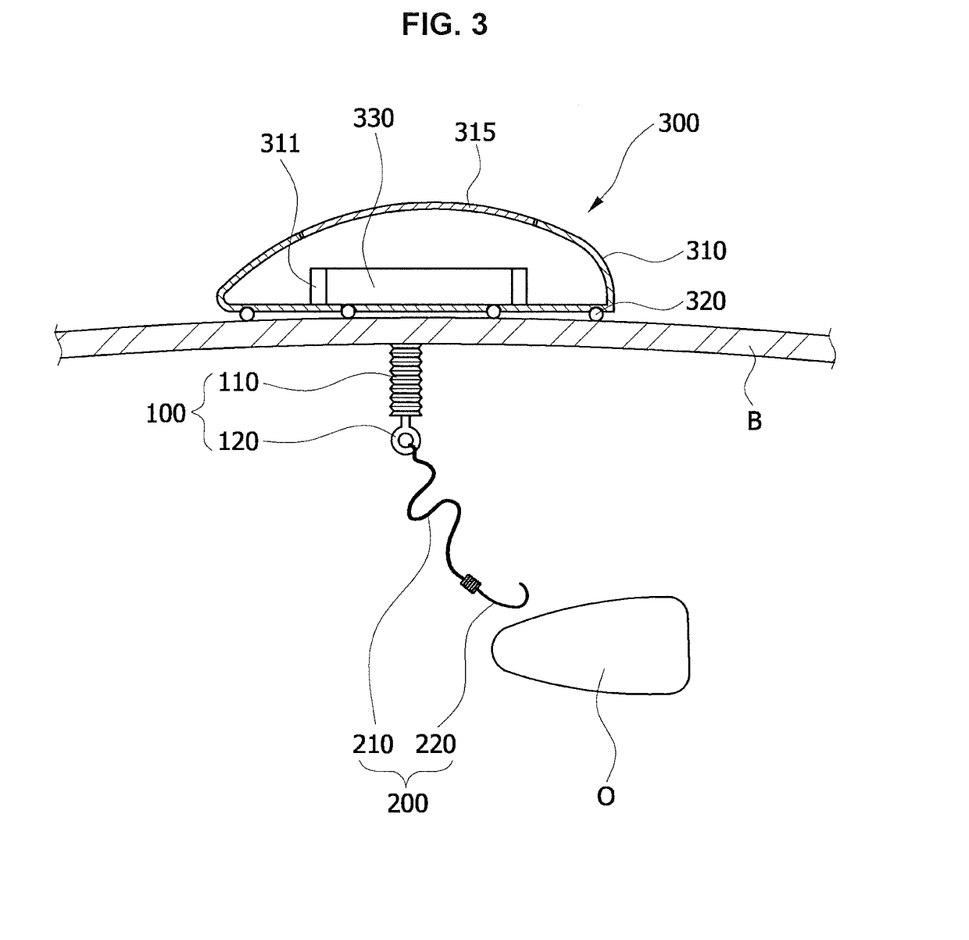
FIG. 3 is a schematic view of a retractor according to one embodiment of the present invention.

Referring to FIGS. 1 to 3, a retractor according to one embodiment of the present invention includes a movable body portion 100, a hook portion 200, and an operating portion 300.

The movable body portion 100 is inserted into a body. As used herein, the phrase "into a (the) body" refers to "into an (the) abdominal wall B". The movable body portion 100 is inserted into the abdominal wall B in advance of surgical instruments.

The movable body portion 100 includes a material creating attractive force between the movable body portion and the operating portion 300 to be moved in association with movement of the operating portion 300.

The movable body portion 100 includes a moving section 110 and a ring section 120. The moving section 110 is formed of a material creating attractive force between the moving section and the operating portion 300. The ring section 120 is connected to a lower side of the moving section 110 (based on FIG. 3) and has a circular ring shape. A string 210 described below is fastened to the ring section 120 by tying or the like.

The hook portion 200 is connected to the movable body portion 100 within the abdominal wall B and pulls an object O such as body organs or tissues. Specifically, the hook portion 200 includes a string 210 and a hook 220.

The string 210 is connected at one side thereof to the movable body portion 100, specifically the ring section 120, and is connected at the other side thereof to the hook 220. The string 210 is freely movable within the abdominal wall B and may be typically formed as a string.

Since the string 210 is freely movable, the string can pull the object O in a desired direction. This is highly advantageous in securing a space for surgery.

Length of the string 210 connected to the movable body portion 100 may be adjusted according to an internal structure of the abdominal wall B and surgical conditions. In other words, since the string 210 is simply configured to be connected to the ring section 120 at one side thereof and connected to the hook 220 at the other side thereof, the length of the string 210 can easily be adjusted by varying a portion of the string connected to the ring section 120 or the hook 220.

In addition, since the string 210 is connected to the ring section 120 by tying the string to the ring section 120, both coupling of the string to the ring section 120 and separation of the string from the ring section 120 can be easily achieved. Thus, when a plurality of strings 210 having different lengths are used, replacement of the string 210 taking an internal structure of the abdominal wall B into account can be easily performed.

Referring to FIGS. 3 to 5, the hook 220 hooks the object O and is connected to the movable body portion 100 through the string 210. Thus, when the string 210 is tightly strained due to tension created by the movement of the movable body portion 100, the hook 220 is moved in a moving direction of the movable body portion 100.

At the same time, as the object O hooked by the hook 220 is also moved in the moving direction of the movable body portion 100, traction of the object O is achieved. It should be understood that traction of the object O is performed to a degree causing no damage to the object O.

The hook 220 has a fish hook shape. Thus, the object O can easily be hooked by the hook 220 using a gripper or the like inserted into an incision or a natural orifice.

The operating portion 300 operates the movable body portion 100 inserted into the abdominal wall B from outside of the abdominal wall B. Since the operating portion 300 operates the movable body portion 100 with the abdominal wall B disposed therebetween, it is important to create an attractive force above a preset value between the operating portion 300 and the movable body portion 100.

For this purpose, the operating portion 300 includes a magnet 330 having magnetism, and the moving section 110 of the movable body portion 100 includes a material capable of being attracted to the magnet 330 such that an attractive force above a preset value can be created between the magnet 330 and the moving section.

As used herein, the term "attractive force above a preset value" means an attractive force which allows the moving section 110 to be moved along a moving path of the operating portion 300 inside the body when the operating portion 300 is moved outside the body.

By way of example, it is necessary for attractive force between the operating portion 300 and the moving section 110 to allow the operating portion 300 to move the moving section 110 freely, even with the abdominal wall B disposed therebetween.

The operating portion 300 further includes a housing 310 and balls 320.

The housing 310 forms a contour of the operating portion 300 and is formed therein with a mounting jaw 311. The mounting jaw 311 surrounds the magnet 330 inserted into the housing 310 to hold the magnet 330 in place.

The housing 310 is provided at an upper side thereof with a door 315. The door 315 closes an open hole formed at the upper side of the housing 310 to block dust or foreign matter from entering the housing 310.

The magnet 330 is detachably mounted within the housing 310, specifically on the mounting jaw 311. Thus, both positioning and replacement of the magnet 330 can be easily achieved.

A need for replacement of the magnet 330 is due to the thickness of the abdominal wall B. In other words, since the thickness of the abdominal wall B varies from person to person, it is necessary to adjust magnitude of magnetism to create an appropriate attractive force between the magnet 330 and the moving section 110. Thus, the magnet 330 is mounted in the mounting jaw 311 to be prevented from being moved inside the housing 310 and to be easily replaced.

The balls 320 are rotatably provided at one side of the housing 310, specifically at an underside of the housing 310 facing the abdominal wall B. Thus, the balls can reduce friction between the housing 310 and the abdominal wall B. As a result, the housing 310, which typically adjoins an outer surface of the abdominal wall B in use, can be smoothly moved.

Although the present invention has been described by way of example wherein one hook portion 200 is connected to the movable body portion 100, the present invention is not limited thereto. Thus, it should be understood that a plurality of hook portions 200 may be connected to the movable body portion 100 at the same time, as shown in FIG. 6. In this case, traction of the object O can be more easily achieved, since the plurality of hook portions 200 shares the traction force.

As described above, the surgical retractor according to the present invention allows organs or tissues inside a body to be pulled by the hook portion inserted in advance of surgical instruments, thereby eliminating a need for a separate incision for traction of organs or tissues.

In addition, the surgical retractor according to the present invention can remotely pull organs or tissues inside the body and thus allows easy access to organs or tissues during surgery whiling securing a clear view for surgery.

Further, the surgical retractor according to the present invention can achieve traction of organs or tissues inside the body only by the string and the hook, and thus allows simplification of a structure of the retractor inserted into a body, thereby reducing time and cost needed to disinfect or replace the retractor.

Although some embodiments have been disclosed above, it should be understood that these embodiments are given by way of illustration only, and that various modifications, variations, and alterations can be made without departing from the spirit and scope of the present invention. Therefore, the scope of the present invention should be limited only by the accompanying claims and equivalents thereof.

What is claimed is:
1. A surgical retractor assembly comprising:
a movable body portion inserted into a body;
a hook portion connected to the movable body portion inside the body and pulling an object inside the body; and
an operating portion moving the movable body portion within the body from outside of the body,
wherein the operating portion comprises a magnet, and the movable body portion comprises a material capable of being attracted to the magnet to be moved inside the body in association with movement of the operating portion,
wherein the operating portion further comprises a housing and a ball rotatably disposed on one surface of the housing, and the magnet is mounted within the housing.

2. The surgical retractor assembly according to claim 1, wherein the magnet is detachably mounted in a mounting jaw formed within the housing.

3. The surgical retractor assembly according to claim 1, wherein the hook portion comprises a string connected to the movable body portion at one side thereof, and a hook connected to the other side of the string and pulling the object.

4. The surgical retractor assembly according to claim 3, wherein, when the movable body portion is moved inside the body through movement of the operating portion outside the body, the object is pulled by the hook due to tension created in the string.

* * * * *